US00PP20753P3

(12) United States Plant Patent
Sheehan

(10) Patent No.: US PP20,753 P3
(45) Date of Patent: Feb. 16, 2010

(54) GRAPEVINE PLANT NAMED 'SHEEGENE-4'

(50) Latin Name: *Vitis vinifera*
Varietal Denomination: Sheegene-4

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 154 days.

(21) Appl. No.: 11/594,527

(22) Filed: Nov. 8, 2006

(65) Prior Publication Data

US 2008/0134382 P1 Jun. 5, 2008

(51) Int. Cl.
*A01H 5/00* (2006.01)

(52) U.S. Cl. ..... Plt./208

(58) Field of Classification Search ..... Plt./207, Plt./208

See application file for complete search history.

(56) References Cited

U.S. PATENT DOCUMENTS

PP4,787 P * 11/1981 Olmo et al. ..... Plt./205
PP18,226 P3 * 11/2007 Gargiulo ..... Plt./205

* cited by examiner

*Primary Examiner*—Wendy C. Haas
(74) *Attorney, Agent, or Firm*—Baker Manock & Jensen, PC; Eric C. Cole, Esq.

(57) ABSTRACT

A new and distinct variety characterized by a large green nearly-seedless grape with excellent flavor that ripens in the second week of September approximately eight weeks later than the 'Thompson Seedless' Grape (unpatented). The berries of this new variety are produced on strong woody stems and branches and are very well adapted to commercial harvesting.

1 Drawing Sheet

Latin name of the genius and species of the plant claimed: *Vitis vinifera.*

Variety denomination: 'Sheegene-4'.

The claimed plant relates to a new and distinct variety of *Vitis vinifera* to be known as 'Sheegene-4'. The new variety was first hybridized by Timothy P. Sheehan of Porterville, Calif. in the spring of 2000; it is highly productive and produces a large green nearly-seedless grape with excellent flavor. The pollen parent is 'Autumn Seedless' (unpatented) and the seed parent is 'Red Globe' (U.S. Plant Pat. No. 4,787). The new variety first flowered in May 2003. The new variety of *Vitis vinifera* was first asexually propagated by Timothy P. Sheehan, grafted on 'Harmony' (unpatented) virus-free rootstock in the dormant season of 2003/2004. Eight vines of the new variety were planted in a variety block of *Vitis Vinifera* in an area near Fowler, Calif. on the west side of Thompson Road north of Adams. The grapes produced by the new variety are larger than the 'Thompson Seedless' (unpatented) and have excellent flavor. The new variety has been shown to maintain its distinguishing characteristics through asexual propagation.

BACKGROUND OF THE INVENTION

The present invention relates to a new and distinct variety of grape which will hereinafter be denominated as 'Sheegene-4' and more particularly as a grapevine which produces a green nearly-seedless table grape that matures during the second week of September in the San Joaquin valley of Central Calif. The new invention most closely resembles Thompson Seedless (unpatented) but it produces a larger grape that is very sweet tasting, has excellent flavor, and matures at least eight weeks later.

SUMMARY OF THE INVENTION

The claimed plant is characterized by producing a large green nearly-seedless grape with excellent flavor that is mature for harvesting and shipment during in the second week of September, and it can be compared to the Thompson Seedless Grape (unpatented) but that it matures about eight weeks later, among other distinguishing characteristics.

BRIEF DESCRIPTION OF THE DRAWING

The accompanying drawing is a color photograph of the grapes produced by the subject variety; several leaves are displayed as well as a typical section of the vine of the subject variety. Across the top of the colored photograph on the left is a small cluster of berries; in the center is a shoot displaying tendrils and small leaves; and to the right is a mature leaf displaying the upper surface and petiole. Across the middle of the colored photograph on the left is a cluster of mature grapes; in the center are four grapes cut in half longitudinally as well as horizontally displaying the flesh and shape; and to the right is a shoot and tendrils including small leaves. Across the bottom of the colored photograph on the left is a mature leaf displaying the lower surface and a mature cane with small leaves displaying the nodes.

DETAILED BOTANICAL DESCRIPTION

Referring more to the horticultural description of the new and distinct variety of grapevine, the following description has been observed under the ecological conditions prevailing at the origin vineyard that is located east of Fowler, Calif. in the San Joaquin Valley of Central Calif.

All major color designations are by reference to the Dictionary of Color by Maerz and Paul, First Edition, published in 1930. Common colors names are also used in several instances.

Vine:

*Size.*—Large for a four year old vine.

*Vigor.*—Very good.

*Chilling Requirements.*—Normal for grapes in San Joaquin Valley of Central Calif.

*Figure.*—With wide cordons forming a "T" shape.

*Production Capacity.*—Very good.

*Regularity of Bearing.*—Regular.

Trunk:

*Size.*—Medium — 13¼ inches (33.7 cm) in circumference, 27 inches above graft.

*Surface Texture.*—Rough, shaggy.

*Color of Bark.*—Pl.7 E9 Kaffa Hamstead Brown. Mature Cane — Color: Pl.13 G10 Pekinese. Nodes — Five on mature canes, 26 inches long (66.4 cm).

*Length Between Nodes.*—12.7 cm (5 inches). Lenticel — Numbers: 0. Lenticel — Size: 0. Shoots — Size: Medium to large. Shoots — Length: 3¼ to 4.5 inches (8.23 to 11.43 cm). Shoots — Shape: Droopy. Tendrils — Numbers: One at nodes. Tendrils — Size: Medium to large; 3¼ to 5 inches (8.23 to 12.7 cm). Tendrils — Location: At node.

*Tendrils Form.*—Bifurcate. Tendrils — Texture: Firm, woody.

*Buds Shape.*—Convex.

*Buds Size.*—Medium; 7 mm (0.28 inches) in length, 5 mm (0.20 inches) in width.

*Buds Fruitfulness.*—Very good.

Branches:

*Size.*—Medium; 6.35 cm (2½ inches) circumference.

*Surface Texture.*—Nearly smooth.

*Cordons.*—40 inches (101.6 cm) from trunk at one side, 34½ inches from trunk on other side. Color — One year or older wood: Pl. 7 E5 Mauve Rose. Color — Immature Branches: Pl.19 L5 — Cosse gr.

Leaves:

*Size.*—Generally large.

*Density.*—Dense.

*Average Length.*—16.0 to 21.3 cm (6⅜ to 9⅛ inches). Average

*Width.*—18.8 to 23.5 cm (7⅞ to 10⅛ inches).

*Shape.*—Pentagonal. Texture — Upper surface: Smooth. Texture — Lower Surface: Glabrous. Color — Upwardly Disposed Surface: Pl.23 J8 Mt. Vernon green. Color — Lower Disposed Surface: Pl.21 I7 Fern. Color — Leaf Vein — Pl.17 K7 Viridine gr.

*Glandular Characteristics.*—0.

*Petiole Size.*—Large.

*Petiole Length.*—15.7 to 18 cm (6 to 7 inches).

*Petiole Thickness.*—9.8 mm (0.39 inches). Petiole Sinus Form — Upside down U-shape.

*Lobes.*—Normally four.

*Tooth Size.*—Medium; 19.1 to 22.2 mm (¾ to ⅞ inches) in width, 16.2 to 28.6 mm (0.638 to 1.126 inches) in length. Tooth — Number: Four large normally between lobes. Tooth — Shape: Convex.

Inflorescence:

*Size.*—11.8 cm (4.65 inches). Number Borne — Per Spur: One to two. Number Borne — Per Vine: Many; 20 to 25.

Flowers: Flower Buds — Size: Small. Flower Buds — Surface: Glabrous. Flower Buds — Quantity: Moderate.

*Date of Bloom.*—May 15, 2006.

*Date of Full Bloom.*—May 20, 2006.

*Size of Bloom.*—5 to 6 mm (0.20 - 0.24 inches).

*Petal Color.*—Pl.20 K6 Piquant green.

*Petal Size.*—Small; 1 to 2 mm (0.039 to 0.078 inches).

*Pistol Color.*—Pl.17 L7 Viridine y.

*Date of First Visible Berries.*—May 20, 2006. Size — Generally: Small; 2 mm (0.079 inches).

Fruit:

*Solids.*—8.9.

*Acid.*—0.38.

*Sugar/Acid Ratio.*—49.7.

*Juice pH.*—3.78.

*Seeds.*—Rudimentary.

*Seed Numbers.*—One to two.

*Capstem Pedicel.*—8 mm (0.31 inches).

*Berry Weight.*—11.36 grams.

*Juice Color.*—Pl.17 A6 Opaline gr.

*Size.*—Large. Cluster — Size: Average length not including main stem; 22 to 23 cm (8.75 inches). Cluster — Average Diameter at Greatest Width: 12.7 cm (5 inches). Cluster — Weight: 681.6 grams (1½ lbs.).

*Compact.*—Compact.

*Cluster Form.*—Conical. Stems — Generally: Large; 6 cm (2.86 inches) in length, approximately 6 mm (0.024 inches) in width.

*Berry Size.*—Large.

*Berry Form.*—Ovate.

*Berry Number.*—Approximately 60 per bunch. Berry Size — Average Dimension in Longitudinal Axis: 30 mm (1.18 inches). Berry Size — Average Dimension in Transverse Axis: 22 mm (0.87 inches).

Skin:

*Thickness.*—Thin.

*Texture.*—Tough.

*Tendency to Crack.*—None.

*Blush Color.*—None.

*Ground Color.*—P1.19 K9 Sea green.

*Pulp.*—Clear.

*Lenticels.*—0.

Flesh:

*Color.*—Pl.17 L7 Viridine y.

*Juice Production.*—Good.

*Flavor.*—Very good.

*Aroma.*—Very mild.

*Texture.*—Firm.

*Ripening.*—Even.

*Eating Quality.*—Very good to excellent.

*Resistance to Disease.*—Unknown.

*Harvesting.*—Second week of September.

*Shipping and Handling Qualities.*—Very good.

I claim:

1. A new and distinct variety of grapevine as herein illustrated and described.

* * * * *

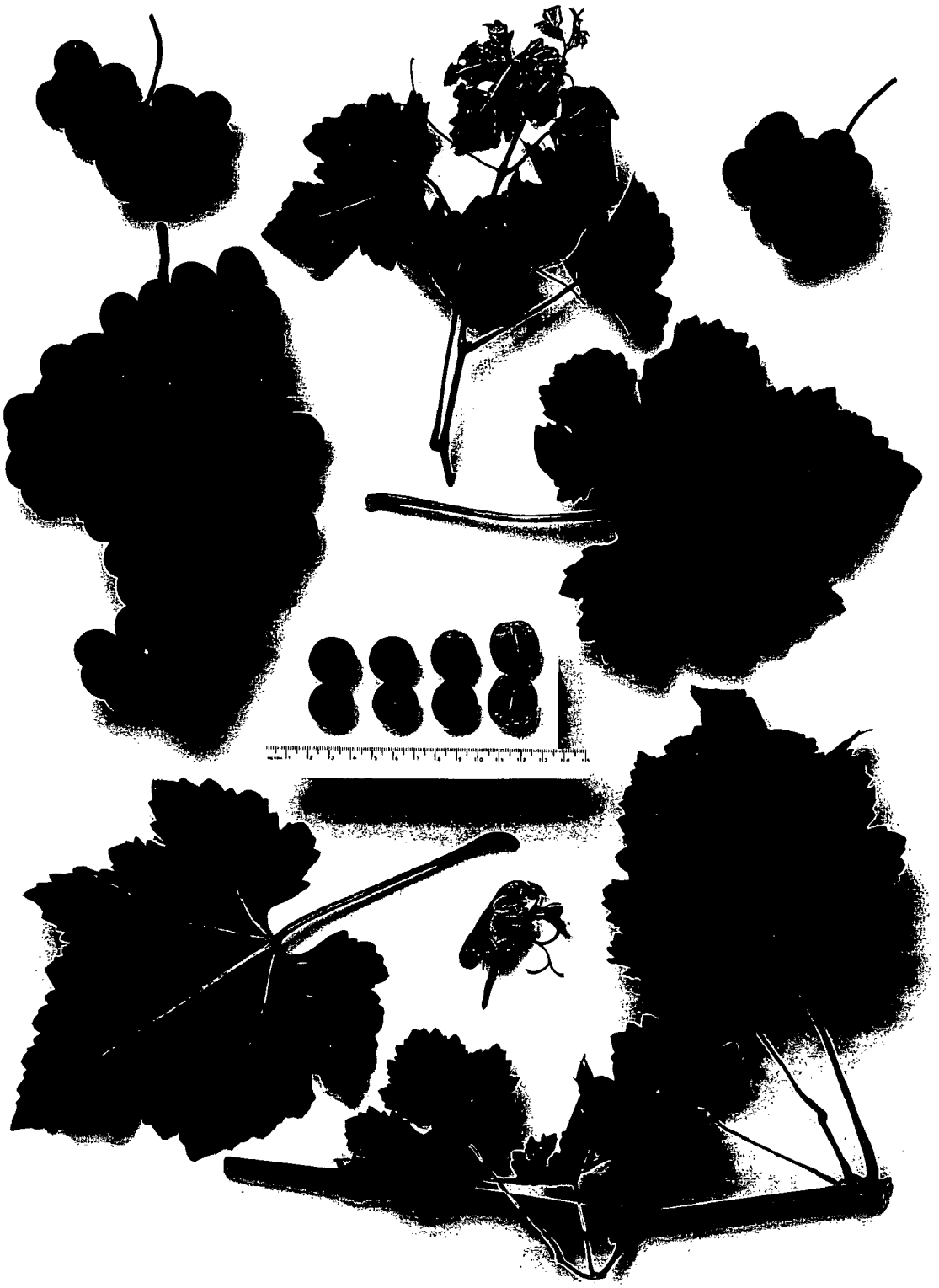

UNITED STATES PATENT AND TRADEMARK OFFICE

CERTIFICATE OF CORRECTION

PATENT NO. : PP20,753 P3
APPLICATION NO. : 11/594527
DATED : February 16, 2010
INVENTOR(S) : Timothy P. Sheehan It is certified that error appears in the above-identified patent and that said Letters Patent is hereby corrected as shown below:

On the Title Page

Column 1, line 9, "'Autumn Seedless' (unpatented)" should be changed to --'Princess' (unpatented)--.

Signed and Sealed this
Twenty-fourth Day of September, 2013

Teresa Stanek Rea
*Deputy Director of the United States Patent and Trademark Office*